United States Patent
Lu et al.

(10) Patent No.: US 9,925,238 B2
(45) Date of Patent: Mar. 27, 2018

(54) USE OF PEPTIDE FOR TREATING ANGIOGENESIS-RELATED DISEASES

(71) Applicants: MacKay Memorial Hospital, Taipei (TW); ASCLEPIUMM TAIWAN CO., LTD., New Taipei (TW)

(72) Inventors: Chi-Sheng Lu, Taipei (TW); Hung-I Yeh, Taipei (TW); Min-Che Chen, New Taipei (TW); Chun-Wei Chen, Taipei (TW)

(*) Notice: Subject to any disclaimer, the term of this patent is extended or adjusted under 35 U.S.C. 154(b) by 0 days.

(21) Appl. No.: 15/307,812

(22) PCT Filed: Apr. 29, 2015

(86) PCT No.: PCT/CN2015/077742
§ 371 (c)(1),
(2) Date: Oct. 29, 2016

(87) PCT Pub. No.: WO2015/165392
PCT Pub. Date: Nov. 5, 2015

(65) Prior Publication Data
US 2017/0042970 A1    Feb. 16, 2017

Related U.S. Application Data

(60) Provisional application No. 61/986,141, filed on Apr. 30, 2014.

(51) Int. Cl.
*A61K 38/08* (2006.01)
*A61K 38/17* (2006.01)
*C07K 14/00* (2006.01)
*A61P 43/00* (2006.01)

(52) U.S. Cl.
CPC .......... *A61K 38/1709* (2013.01); *A61K 38/08* (2013.01); *C07K 14/00* (2013.01)

(58) Field of Classification Search
CPC ..... A61K 38/1709; A61K 38/08; C07K 14/00
See application file for complete search history.

(56) References Cited

U.S. PATENT DOCUMENTS

2012/0276082 A1* 11/2012 Chen .................... C07K 14/705
424/130.1

OTHER PUBLICATIONS

Gupta et al, Angiogenesis: a curse or cure?, Postgrad Med J, 2005, 81, pp. 236-242.*
Potente et al, Basic and Therapeutic Aspects of Angiogenesis, Cell, 2011, 146, pp. 873-887.*
Kieran et al, The VEGF Pathway in Cancer and Disease: Responses, Resistance, and the Path Forward, Cold Spring Harb Perspect Med, 2012, pp. 1-17.*
Farjo et al, The potential of nanomedicine therapies to treat neovascular disease in the retina, Journal of Angiogenesis Research, 2010, 2, pp. 1-14.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Yampolsky et al, The Exchangeability of Amino Acids in Proteins, Genetics, 2005, 170, pp. 1459-1472.*

* cited by examiner

*Primary Examiner* — Julie Ha
*Assistant Examiner* — Li N Komatsu (57) ABSTRACT

Disclosed herein are methods for treating an angiogenesis-related condition or disease in a subject in need thereof. Said method includes administering to the subject a peptide having at least 90% sequence identity of the sequence of SEQ ID NO: 1 or SEQ ID NO:3 in a therapeutically effective amount.

4 Claims, 10 Drawing Sheets
(3 of 10 Drawing Sheet(s) Filed in Color)

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: Dsg2-derived peptide

<400> SEQUENCE: 1

Lys Ile Asn Ala Thr Asp Ala Asp Glu Pro Asn Thr Leu Asn Ser Lys
1               5                   10                  15

Ile Ser Tyr Arg Cys
            20
```

```
<210> SEQ ID NO 2
<211> LENGTH: 20
<212> TYPE: PRT
<213> ORGANISM: Artificial Sequence
<220> FEATURE:
<223> OTHER INFORMATION: scramble peptide

<400> SEQUENCE: 2

Lys Asn Ile Thr Ala Ala Asp Glu Asp Asn Pro Leu Thr Ser Asn Lys
1               5                   10                  15

Ile Tyr Ser Arg
            20

<210> SEQ ID NO 3
<211> LENGTH: 10
<212> TYPE: PRT
<213> ORGANISM: Artificial Sequence
<220> FEATURE:
<223> OTHER INFORMATION: IP10

<400> SEQUENCE: 3

Ile Val Ser Leu Glu Pro Ala Tyr Pro Pro
1               5                   10

<210> SEQ ID NO 4
<211> LENGTH: 113
<212> TYPE: PRT
<213> ORGANISM: Homo sapiens

<400> SEQUENCE: 4

Gln Asp Val Phe Val Gly Ser Val Glu Glu Leu Ser Ala Ala His Thr
1               5                   10                  15

Leu Val Met Lys Ile Asn Ala Thr Asp Ala Asp Glu Pro Asn Thr Leu
            20                  25                  30

Asn Ser Lys Ile Ser Tyr Arg Ile Val Ser Leu Glu Pro Ala Tyr Pro
        35                  40                  45

Pro Val Phe Tyr Leu Asn Lys Asp Thr Gly Glu Ile Tyr Thr Thr Ser
    50                  55                  60

Val Thr Leu Asp Arg Glu Glu His Ser Ser Tyr Thr Leu Thr Val Glu
65                  70                  75                  80

Ala Arg Asp Gly Asn Gly Glu Val Thr Asp Lys Pro Val Lys Gln Ala
                85                  90                  95

Gln Val Gln Ile Arg Ile Leu Asp Val Asn Asp Asn Ile Pro Val Val
            100                 105                 110

Glu
```

USE OF PEPTIDE FOR TREATING ANGIOGENESIS-RELATED DISEASES

CROSS-REFERENCE TO RELATED APPLICATIONS

This application is a 371 application of PCT/CN2015/077742 filed on Apr. 29, 2015, which claims the benefit of U.S. Provisional Application No. 61/986,141, filed on Apr. 30, 2014.

BACKGROUND OF THE INVENTION

Field of the Invention

The present disclosure relates to the medical field. More particularly, the disclosed invention relates to the use of a desmoglein 2-derived peptide for treating angiogenesis-related diseases.

Description of Related Art

Angiogenesis is the formation of new capillaries from pre-existing blood vessels. It is a sophisticated process, regulated by the balance between endogenous, pro-angiogenic (or stimulatory) and anti-angiogenic (or inhibitory) factors. A number of pro-angiogenic factors have been identified, non-exclusive examples of which include basic fibroblast growth factor (bFGF), interleukin 1 (IL-1), IL-4, IL-6, IL-8, vascular endothelial growth factor (VEGF), transforming growth factor beta 1 (TGFb1), matrix metalloproteinase-2 (MMP-2), MMP-9, epidermal growth factor (EGF), tumor necrosis factor (TNF), myeloid growth factor (MGF), angiogenin, angiotropin, plasminogen activator, proteases, hepatocyte growth factor, insulin-like growth factor, prostaglandin E, hypoxaemia, and macrophages derived P factor. Exemplary anti-angiogenic factors include, interferons, thrombospondin, angiostatin, endostatin, IL-10, IL-12, platelet-derived factor, vascular endothelial growth inhibitor (VEGI), tissue matrix metalloproteinase inhibitors (MMPI), and plasminogen activator inhibitor.

Upon the activation by one or more pro-angiogenic factor or by the pro-angiogenic signal(s) derived therefrom, endothelial cells resting in the parent vessels synthesize and release degrading enzymes allowing the endothelial cells to migrate, proliferate and finally differentiate to give rise to blood vessels. Physiological angiogenesis normally takes place during embryonic and fetal organogenesis, reproductive cycle (e.g., female menstrual cycle), repair processes, wound healing processes and tissue regeneration. However, in many pathological conditions, the disease appears to be associated with upregulated angiogenesis.

The diseases associated with upregulated or abnormal angiogenesis include: (1) ocular neovascular disease (such as, retinal neovascular disease, neovascular age-related macular degeneration, diabetic retinopathy, and retinopathy of prematurity), a disease characterized by invasion of new blood vessels into the retina or cornea, leading to irreversible visual impermanent; (2) rheumatoid arthritis and osteoarthritis; the cells within subchondral spaces and vascular channels, and the chondrocytes secrete various growth factor that induce angiogenesis, which may result in the pathogenesis of synovitis and the subsequent destruction of the articular cartilage; (3) inflammation and inflammatory disease; during inflammation, the inflammatory cytokines (such as cyclooxygenase 2, prostaglandin E2, and thromboxane A2), the inflammatory cells (such as macrophage, T cell, and mast cell), and the hypoxia-inducible factor (HIF) elicit the expression of pro-angiogenic factors that cause angiogenesis; the newly formed vasculature in turn enhance the infiltration of the inflammatory cells, which further deteriorate the inflammation; (4) hereditary diseases, such as Osler-Weber-Rendu disease or hereditary hemorrhagic telangiectasia, are related to the disorder of angiogenesis, in which a multisystemic angiodysplasia is responsible for severe hemorrhage; and (5) tumor formation and metastasis; tumor cells secret various pro-angiogenic factors that promote the formation of new blood vessels via angiogenesis process; the new blood vessels are important in tumor growth by providing tumor cells adequate nutrients and oxygen, and are correlated with tumor metastasis by providing a route for tumor migration and invasion.

In view of the foregoing, there exists a need in the art for providing novel medicaments and methods capable of inhibiting angiogenesis and/or treating angiogenesis-related diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least in part, on the discovery that a short peptide derived from desmoglein 2 (Dsg2) protein can inhibit angiogenesis. Therefore, the first aspect of the present disclosure pertains to the use of the Dsg2-derived peptide for the preparation of a medicament for treating an angiogenesis-related condition and/or disease in a subject.

As angiogenesis is involved in the development and progress of different diseases, and based on the anti-angiogenic efficacy of the Dsg2-derived peptide, the second aspect of the present disclosure thus pertains to a method for treating an angiogenesis-related condition and/or disease in a subject. The method comprises the step of administering to the subject a therapeutically effective amount of Dsg2-derived peptide so as to alleviate or ameliorate symptoms of the angiogenesis-related condition and/or disease.

According to various embodiments of the present disclosure, the Dsg2-derived peptide may have at least 90% sequence identity to SEQ ID NO: 1 or SEQ ID NO: 3. In certain embodiments, the sequence identity can be at least 95%. In one specific embodiment, the sequence of the Dsg2-derived peptide is identical to the sequence of SEQ ID NO: 1. In another specific embodiment, the sequence of the Dsg2-derived peptide is identical to the sequence of SEQ ID NO: 3.

According to some embodiments of the present disclosure, the subject is a mammal, such as human.

In various embodiments, the angiogenesis-related condition and/or disease is or is caused by an ocular angiogenic disease, inflammation or inflammatory disease, tumor, tumor metastasis, infection, cardiovascular disease, or injury.

Non-limiting examples of the ocular angiogenic disease are retinal neovascular disease, neovascular age-related macular degeneration, juvenile macular degeneration, diabetic retinopathy, retinopathy of prematurity, corneal graft rejection, corneal diseases, neovascular glaucoma, retrolental fibroplasia, neovascular glaucoma, conjunctivitis, keratitis, rubeosis, retinitis, choroiditis, Vitamin A deficiency, contact lens overwear, pterygium, phylectenulosis, chemical burns, scleritis, Terrien's marginal degeneration, retinal detachment, pars planitis, Eales disease, or post-laser complications.

Examples of the inflammation or inflammatory disease include, but are not limited to, rheumatoid arthritis, osteoarthritis, psoriasis, sjogren's syndrome, acne rosacea, systemic lupus, Wegeners sarcoidosis, polyarteritis, scleroderma, Crohn's disease, and Bartonellos.

Tumors treatable by the present method include lung carcinoma, breast carcinoma, ovarian carcinoma, skin carcinoma, colon carcinoma, urinary bladder carcinoma, liver carcinoma, gastric carcinoma, kidney carcinoma, prostate cancer, pancreatic cancer, renal cell carcinoma, nasopharyngeal carcinoma, squamous cell carcinoma, thyroid papillary carcinoma, cervical carcinoma, small cell lung carcinoma, non-small cell lung carcinoma, head and neck squamous cell cancer, brain tumor, sarcomas, melanoma, hemangioma and leukemia.

Infections by bacteria, viruses, fungi, or protozoans that involve angiogenesis are also within the scope of the present method.

Non-exhaustive examples of cardiovascular disease are atherosclerosis, myocardial angiogenesis, hyperviscosity syndromes, vein occlusion, artery occlusion, carotid obstructive disease, and Osler-Weber-Rendu disease.

According to various embodiments of the present disclosure, the Dsg2 peptide is administered to the subject in an amount effective to elicit an anti-angiogenic effect, and should exhibit a therapeutic effect.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where:

FIG. 1 present photographs illustrating the 3D structure of the EC2 domain of Dsg2 peptide (SEQ ID NO: 4) according to Example 1 of the present disclosure;

FIG. 2 presents the data illustrating the tube formation of human endothelial progenitor cells (EPCs) on Matrigel (left panel) and the relative tube length of the forming tube according to Example 1 of the present disclosure;

FIG. 3 present photographs illustrating the tube formation of human endothelial progenitor cells (EPCs) on Matrigel according to Example 2 of the present disclosure;

FIG. 4 is a histogram depicting the relative tube length of tube formed on the Matrigel according to Example 2 of the present disclosure;

FIG. 5 are photographs illustrating the tube formation of human umbilical vein endothelial cells (HUVECs) on Matrigel according to Example 3 of the present disclosure;

FIG. 6 is a histogram depicting the relative tube length of tube formed on the Matrigel according to Example 3 of the present disclosure;

FIG. 7 present photographs illustrating the newly formed blood vessels in the Matrigel plugs according to Example 4 of the present disclosure;

FIG. 8 is a histogram depicting the hemoglobin content recovered from the Matrigel plug according to Example 4 of the present disclosure;

FIG. 9 are fluorescent photographs illustrating the immunostaining results, in which the endothelial cells of mouse retina are stained with fluorescein-conjugated isolectin B4 and detected by an fluorescence microscope according to Example 5 of the present disclosure; and FIG. 10 is a histogram depicting the percentage of neovascular area in mouse retina according to Example 5 of the present disclosure.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which this invention belongs.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "angiogenesis-related condition and/or disease" means pathological conditions and/or diseases that involve up-regulated angiogenesis for the disease progression or symptom manifestation.

"Percentage (%) amino acid sequence identity" with respect to the amino acid sequences identified herein is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). Specifically, the percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

As discussed herein, minor variations in the amino acid sequences of proteins/peptides are contemplated as being encompassed by the presently disclosed and claimed inventive concept(s), providing that the variations in the amino acid sequence maintain at least 90%, such as at least 91%, 92%, 93%, 94%, 95%, 96%, 97%, 98% and 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of proteins/peptides can be readily prepared by those of ordinary skill in the art. Preferred amino- and carboxy-termini of fragments or analogs occur near boundaries of functional domains.

Unless contrary to the context, the term "treatment" are used herein to refer to curative or palliative measure that results in a desired pharmaceutical and/or physiological effect. Preferably, the effect is therapeutic in terms of partially or completely curing angiogenesis-related conditions and/or diseases. Also, the terms "treatment" and "treating" as used herein refer to application or administration of the present Dsg2-derived short peptide or medicament comprising the same to a subject, who has an angiogenesis-related condition and/or disease, a symptom thereof, a disease or disorder secondary thereto, or a predisposition toward, with the purpose to partially or completely alleviate, ameliorate, relieve, delay onset of, inhibit progression of, reduce severity of, and/or reduce incidence of one or more symptoms or features of the angiogenesis-related condition and/or disease.

The term "effective amount" as used herein refers to the quantity of a component (e.g., a Dsg2-derived short peptide) or medicament comprising the same which is sufficient to yield a desired "effective treatment" as defined hereinabove. The specific therapeutically effective amount will vary with factors such as the particular condition being treated, the physical condition of the patient (e.g., the patient's body mass, age, or gender), the type of mammal or animal being treated, the duration of the treatment, the nature of concurrent therapy (if any), and the specific formulations employed. An effective amount is also one in which any toxic or detrimental effects of the compound or composition are outweighed by the therapeutically beneficial effects. Effective amount may be expressed, for example, as the total mass of the medicament (e.g., in grams, milligrams or micrograms) or a ratio of mass of the medicament to body mass, e.g., as milligrams per kilogram (mg/kg). Persons having ordinary skills could calculate the human equivalent dose (HED) for the medicament (such as the present aster extract) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "therapeutically effective amount" refers to the quantity of the active component or the medicament comprising the same, when administered to a subject in need thereof, is sufficient to yield a desired therapeutic response. A therapeutically effective amount is also one in which any toxic or detrimental effects of the active component or the medicament comprising the same are outweighed by the therapeutically beneficial effects.

The term "subject" refers to a mammal including the human species that is treatable with the present Dsg2-derived peptide or the medicament comprising the same. The term "subject" is intended to refer to both the male and female gender unless one gender is specifically indicated.

The present invention is based on the finding that a short peptide derived from desmoglein-2 (Dsg2) is capable of reducing angiogenesis. Human Dsg2 protein belongs to the family of desmosomal cadherins, which involve in various biological processes including cell adhesion, morphogenesis, cytoskeletal organization and cell sorting/migration, as well as in pathological conditions such as cancer. Dsg2 is required during the signaling pathway of angiogenesis, and prior researches indicate that inhibition of Dsg2 by DSG2-siRNA impaired actin stress fibres formation, capillary morphogenesis in vitro and angiogenesis in vivo.

US patent publication 2012/0276082 (hereinafter, the '082 publication) teaches that certain short peptides derived from Dsg2 reduce the epithelial-mesenchymal transition (EMT) in cells. EMT is a process in which cell mobility is increased due to the loss of cell adhesion, thereby resulting in cells with mesenchymal characteristics. This process is essential for many mesoderm formation, as well as neural tube formation. EMT also plays a central role during tumor progression, invasion and metastasis. Nonetheless, the '082 publication is silent on the anti-angiogenic effect of the Dsg2-derived short peptides. Further, the inventor unexpectedly discovers that the present Dsg2-derived short peptide (e.g., the peptide of SEQ ID NO: 1 and SEQ ID NO: 3) is effective in inhibiting angiogenesis, and the inhibitory efficacy of the peptide of SEQ ID NO: 1 is greater than that of the well-known angiogenesis inhibitor, Bevacizumab (trade name Avastin, Genentech/Roche).

Accordingly, in one aspect, the present disclosure is directed to a use of the Dsg2-derived short peptide for the preparation of a medicament for treating an angiogenesis-related condition and/or disease in a subject. The Dsg2-derived short peptide and/or the medicament containing the same can be applied in a method for inhibiting angiogenesis in a subject, and a method for treating angiogenesis-related conditions and/or diseases.

According to various embodiments of the present disclosure, the method for treating an angiogenesis-related condition and/or disease in a subject in need thereof, comprising the step of administering to the subject a peptide having at least 90% sequence identity to SEQ ID NO: 1 or SEQ ID NO: 3 in a therapeutically effective amount to inhibit angiogenesis at a target site of the subject and exhibit a therapeutic effect.

In various embodiments of the present disclosure, the Dsg2-derived short peptide has at least 90% identity to the amino acid sequence of SEQ ID NO: 1 or SEQ ID NO: 3; for example, the identity can be 90%, 91%, 92%, 93%, 94%, 95%, 96%, 97%, 98%, 99%, or 100%. Preferably, the identity is at least 95%. In one specific embodiment, the Dsg2-derived short peptide is 100% identical to the amino acid sequence of SEQ ID NO: 3. Most preferably, the Dsg2-derived short peptide is 100% identical to the amino acid sequence of SEQ ID NO: 1.

The Dsg2-derived short peptides of the present invention can be synthesized by commonly used methods such as t-BOC or FMOC protection of alpha-amino groups. Both methods involve stepwise syntheses whereby a single amino acid is added at each step starting from the C terminus of the peptide. Peptides of the invention can also be synthesized by the well-known solid phase peptide synthesis methods.

The present Dsg2-derived short peptide is capable of inhibiting the in vivo, ex vivo, or in vitro angiogenesis. Angiogenesis is a complex development process involving the steps of basement membrane degradation, endothelial cell and/or endothelial progenitor cell proliferation, endothelial cell and/or endothelial progenitor cell migration, and tube formation. Endothelial cells form the inner lining of a blood vessel; during an angiogenesis process, the extracellular matrix is degraded, and the endothelial cells are released from the basement membrane. Endothelial progenitor cells are a population of rare cells that circulate in the blood with the ability to differentiate into endothelial cells. In the angiogenesis process, the endothelial cells and the endothelial progenitor cells migrate toward the angiogenic stimuli followed by aligning, branching, and finally forming the tubular polygonal networks of blood vessels. Each of the steps can be a target for intervention, and be measured by various in vitro assays. For example, the in vitro assay used to measure cell proliferation can be thymidine incorporation assay, trypan blue staining, MTT assay, or flow cytometry. The in vitro assay useful in determining cell migration includes Boyden chamber, cell movement assay (also known as phagokinetic track assay), and gap closure assay (also known as wound healing assay). As to the measurement of the ability of endothelial cells to form three-dimensional structures (i.e., tube formation), endothelial cells are generally first seeded on an appropriate extracellular matrix component, such as the Engelbreth-Holm-Swarm (EHS) matrix, the formation of tight junctions is then confirmed and analyzed by electron microscopy. Aside from the in vitro assays, several ex vivo and in vivo assays have also been developed that permit a more realistic appraisal of the angiogenic response than can be obtained in vitro. The ex vivo assays include aortic ring assay, and chick aortic arch assay; and the in vivo assessment of angiogenesis can be performed by chick chorioallantoic membrane (CAM) assay, Matrigel plug assay, sponge implantation assay, corneal angiogenesis assay, and retinal angiogenesis assay.

In the present disclosure, different assays are employed to evaluate the anti-angiogenic efficacy of the present Dsg2-derived short peptide. According to one embodiment, tube formation assay is used, in which the present Dsg2-derived short peptide can reduce the tube length formed by either endothelia cells or endothelial progenitor cells.

According to another embodiment, Matrigel, a gelatinous EHS protein mixture resembling the complex extracellular environment of biological tissue, is used. In the embodiment, the present Dsg2-derived short peptide exhibits the anti-angiogenic efficacy in inhibits the blood vessel formation in Matrigel.

According to still another embodiment, retinal angiogenesis assay is employed, in which the present Dsg2-derived short peptide efficiently suppresses the retinal neovascularization.

According to any of the above-mentioned embodiments, the Dsg2-derived short peptide is present in an effective amount sufficient to inhibit the angiogenesis.

According to some embodiments of the present disclosure, suitable concentration of the present Dsg2-derived short peptide used to inhibit endothelial cell/endothelial progenitor cell proliferation, migration and tube formation is about 0.1-10 mg/ml; that is, the concentration can be 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, or 10 mg/ml. Preferably, the concentration is about 0.5-5 mg/ml. In one specific embodiment, the concentration is 0.5-1 mg/ml.

As to suppress angiogenesis in a subject, the therapeutically effective amount of the present Dsg2-derived short peptide is about 0.1-100 mg/kg body weight of the subject; for example, the therapeutic amount can be 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 20.0, 30.0, 40.0, 50.0, 60.0, 70.0, 80.0, 90.0, or 100.0 mg/kg body weight, dependent on the treatment condition or the physical condition of the subject. According to one embodiment, the present Dsg2-derived short peptide is administered in an amount of about 0.5-50 mg/kg body weight of the subject. In one specific embodiment, 0.5-10 mg/kg body weight is sufficient to inhibit the angiogenesis.

According to one embodiment of the present disclosure, the present Dsg2-derived short peptide is administered to a subject with an angiogenesis-related disease and/or condition, in which the present Dsg2-derived short peptide can efficiently inhibit the pathological angiogenesis and accordingly treat the angiogenesis-related disease and/or condition, while does not affect the physiological angiogenesis (i.e., repair processes, wound healing processes and tissue regeneration) of the subject.

Avastin is an angiogenesis inhibitor, which blocks the signal transduction pathway mediated by VEGF, and thus suppresses the growth of new blood vessels. Avastin is approved by US Food and Drug Administration (FDA) for certain cancers, including colon cancer, lung cancer, renal cancer, ovarian cancer, and glioblastoma multiforme of the brain. According to one specific embodiment of the present disclosure, the present Dsg2-derived short peptide exhibits more effective than Avastin in inhibiting angiogenesis.

In addition to the present Dsg2-derived short peptide, the prepared medicament might further comprise a pharmaceutically acceptable carrier so as to provide a form for proper administration to a living mammal, including human. For example, the pharmaceutically acceptable carrier may be any of a liquid, gel, cream, ointment, adhesive, amniotic membrane, skin substitute, artificial skin, or skin equivalents. Some examples of substances which can serve as pharmaceutically acceptable carriers are gelatin, excipients, pyrogen-free water, isotonic saline, and phosphate buffer solutions.

The choice of a pharmaceutically-acceptable carrier to be used in conjunction with the present Dsg2-derived short peptide is basically determined by the way the medicament is to be administered. The medicament of the present invention may be administered locally (e.g., topically, subconjunctivally, intra-articularly, or intradermally) or systemically (e.g. intravenously or subcutaneously).

Suitable pharmaceutically-acceptable carriers for topical application include those suitable for use in liquids (including solutions and lotions), creams, gels, and the like. Advantageously, the medicament is sterile and can be in dosage unit form, e.g., suitable for topical ocular use. The medicament can be packaged in a form suitable for metered application, such as in container equipped with a dropper. In one embodiment, the pharmaceutically acceptable carrier comprises an ophthalmically acceptable pharmaceutical excipient. In one embodiment, the medicament is a solution prepared using a physiological saline solution as a carrier. In another embodiment, the medicament is an ointment containing the Dsg2-derived short peptide at a suitable concentration. The pH of the solution or ointment is, preferably, maintained between 4.5 and 8.0 using an appropriate buffer system. A neutral pH is more preferred. Alternatively, the Dsg2-derived short peptide may be incorporated in an amniotic membrane, skin substitute, artificial skin, or other skin equivalents that are suitable to be applied to the wound site.

For injection (including topical, enteral and parenteral injection), the Dsg2-derived short peptide may be formulated with a pharmaceutically acceptable carrier such as a sterile aqueous solution which is preferably isotonic with the blood of the recipient. Such formulations may be prepared by dissolving or suspending the solid active ingredient in water containing physiologically compatible substances such as sodium chloride, glycine, and the like, and having a buffered pH compatible with physiological conditions to produce an aqueous solution, and rendering said solution sterile.

Other diluents or solvent suitable for manufacturing sterile injectable solution or suspension include, but are not limited to, 1,3-butanediol, mannitol, water, and Ringer's solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as polysorbate-type nonionic surfactant TWEEN or sorbitan ester-type nonionic surfactant SPANS, or other similar emulsifying agents or bioavailability enhancers that are commonly used in manufacturing pharmaceutically acceptable dosage forms can also be used for the purpose of formulation.

Medicament of the invention can also comprise various additives known to those skilled in the art. For example, solvents, including relatively small amounts of alcohol, may be used to solubilize certain drug substances. Other optional pharmaceutically-acceptable additives include ° pacifiers, antioxidants, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Permeation enhancers and/or irritation-mitigating additives may also be included in the medicament of the present invention.

According to some embodiments of the present disclosure, the subject is a mammal, such as human.

Angiogenesis-related diseases treatable by the present methods including ocular angiogenic diseases, inflammation or inflammatory diseases, tumor, tumor metastasis, infections, cardiovascular diseases, and injuries. As could be appreciated by persons having ordinary skill in the art, the above-mentioned categories are provided for the purposes of illustration while not intending to provide clinical classification of diseases. Specifically, a given condition/disease described in a specific disease category may also fit the general definition of another disease category. For example, keratitis, albeit being listed as an ocular angiogenic disease in the present disclosure, is often caused by bacterial, fungal or viral infection, and usually involves inflammation.

There are various ocular conditions and/or diseases manifest excess growth of blood vessels; non-limiting examples thereof include, retinal neovascular disease, neovascular age-related macular degeneration, juvenile macular degeneration, diabetic retinopathy, retinopathy of prematurity, corneal graft rejection, corneal diseases, neovascular glaucoma, retrolental fibroplasia, neovascular glaucoma, conjunctivitis, keratitis, rubeosis, retinitis, choroiditis, Vitamin A deficiency, contact lens overwear, pterygium, phylectenulosis, chemical burns, scleritis, Terrien's marginal degeneration, retinal detachment, pars planitis, Eales disease, or post-laser complications.

Certain symptom of inflammation may lead to angiogenesis at the inflammatory site, and hence, angiogenesis-related diseases also comprise some inflammatory disorders such as, rheumatoid arthritis, osteoarthritis, psoriasis, sjogren's syndrome, acne rosacea, systemic lupus, Wegeners sarcoidosis, polyarteritis, scleroderma, Crohn's disease, and Bartonellosis.

Angiogenesis plays a role in tumor progression and metastasis. Examples of tumor include, but are not limited to, lung carcinoma, breast carcinoma, ovarian carcinoma, skin carcinoma, colon carcinoma, urinary bladder carcinoma, liver carcinoma, gastric carcinoma, kidney carcinoma, prostate cancer, pancreatic cancer, renal cell carcinoma, nasopharyngeal carcinoma, squamous cell carcinoma, thyroid papillary carcinoma, cervical carcinoma, small cell lung carcinoma, non-small cell lung carcinoma, head and neck squamous cell cancer, brain tumor, sarcomas, melanoma, hemangioma and leukemia.

Infections by bacteria, viruses, fungi, or protozoans that involve angiogenesis are also within the scope of the present method.

Factors associated with angiogenesis may also have a role in cardiovascular diseases, such as atherosclerosis, myocardial angiogenesis, hyperviscosity syndromes, vein occlusion, artery occlusion, carotid obstructive disease, and Osler-Weber-Rendu disease.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Materials and Methods

Dsg2-Derived Short Peptide

Dsg2-derived short peptide having the sequence of SEQ ID NO: 1 (KINATDADEPNTLNSKISYRC), scramble peptide from human gene (SEQ ID NO: 2, KNITAADEDNPLTSNKIYSR), and short peptide having the sequence of SEQ ID NO: 3 (IVSLEPAYPP) were synthesized by Genimics BioSci &Tech (Taipei).

Cells

Human umbilical vein endothelial cells (HUVECs) were purchased from PromoCell (Heidelberg). Human endothelial progenitor cells (EPCs) were prepared from healthy donors according to the principles outlined in the Declaration of Helsinki for use of human tissue. This research involved human participants, and ethical approval was granted by the Institutional Review Board of the Mackay Memorial Hospital, New Taipei City, Taiwan (R.O.C.).

Other Materials

Matrigel was purchased from BD Biosciences (Franklin Lakes); and Avastin was obtained from Genetech/Roche (South San Francisco).

Matrigel Angiogenesis Assay

A total of 200 μl Matrigel was added into wells of a 24-well plate and polymerized for 30 minutes at 37° C. EPC suspensions containing various concentrations of Dsg2 peptide (0.25 mg/ml, 0.5 mg/ml, or 1 mg/ml), scramble peptide (1 mg/ml) or Avastin (10 μg/ml) were plated on the Matrigel-coated wells at a density of $5 \times 10^4$ cells (EPCs, or HUVECs) in MV2 medium containing 2% FBS for 24 hours at 37° C. in a 5% $CO_2$ humidified incubator. Each sample was tested in triplicate in the same plate, and wells were photographed with a Leica camera (×40 magnification).

Relative Tube Length

Tube length in relative to the control was quantified by measuring tubes in 5 randomly chosen fields from each well with QWIN software. Experiments were repeated more than three times. The values were expressed as the means±S.D. for the three independent experiments.

Matrigel Plug Assay 0.5 ml of growth factor-reduced liquid Matrigel respectively containing: (1) heparin (60 U/mL); (2) heparin (60 U/mL), VEGF (10 ng/ml), and PBS; (3) heparin (60 U/mL), VEGF (10 ng/ml), and scramble peptide (1 mg/ml); and (4) heparin (60 U/mL), VEGF (10 ng/ml), and Dsg2 peptide (1 mg/ml) were subcutaneously injecting into the skin near the abdominal midline of C57BL/6 mice. 7 days after injection, mice were euthanized, and Matrigel plugs were surgically removed and analyzed.

Hemoglobin Content

For macroscopic analysis of angiogenesis, hemoglobin content in Matrigel was measured with Drabkin reagent 525 (Sigma-Aldrich). Briefly, the Matrigel plug sample was re-liquefied by being place at 4° C. on ice with red cell lysis reagent for 24 hours. After brief centrifugation, 20 μl of supernatant was added to 100 μl of Drabkin solution. The mixture was allowed to stand 30 minute at room temperature, and the absorbance was measured at 540 nm. The obtained hemoglobin content was normalized to the plug weight and the value was expressed as μg hemoglobin/mg Matrigel plug.

Animal Experiment

The neonatal mouse (C57BL/6) pups of normoxia group (serving as control) were kept in room air until postnatal day 12 (P12), while the pups of OIR group were maintained with their nursing mothers for 5 days in 75% oxygen at P7 and then returned to room air (relative hypoxia) so as to generate oxygen-induced neovascularization at P12. 1 μl of Dsg2 peptide (25 μg), scramble peptide (25 μg) and Avastin (10 μg) were intravitreally injected into mouse eyes at P12, respectively. The animals were killed, and the mouse eyes were enucleated at P17.

Whole Mount Immunofluorescent Staining

Mouse eye cups were fixed in 4% paraformaldehyde for 2 hours. The retina was carefully separated from eye cup, and then incubated with fluorescein-labeled isolectin-B4 (Life technologies) at 4° C. overnight. Samples were coverslipped with Vectashield medium (Vector Laboratories), and the lectin labeling was examined by use of the 20× objective of a Zeiss LSM-510 confocal microscope. Fluorescence volume measurements were recorded by creating image stacks of optical slices within lesions with QWIN software. Values for implicit volume were designated as mean total surface area.

Example 1 Identification of Dsg2 Peptide Fragment

Figure 1:
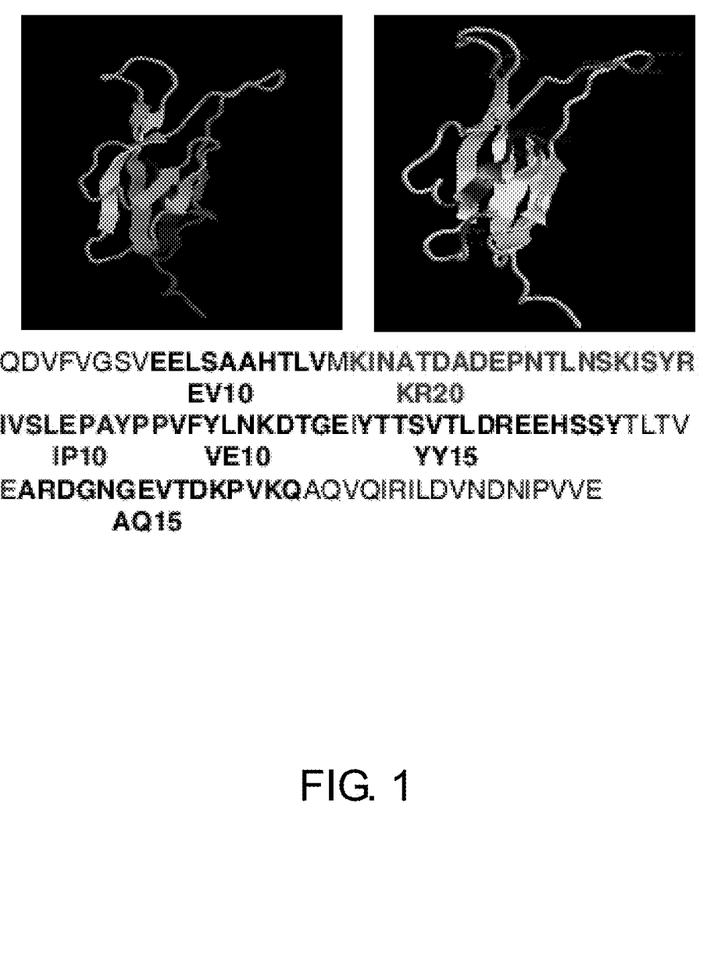

The 3D structure of the EC2 domain of Dsg2 peptide is predicted by using SWISS-MODEL, which indicated that the non-CAR domains containing three loops with anchor residues seeming to be important in biological functions. The EC2 domain of Dsg2 peptide is presented by Rasmol software (FIG. 1), which illustrated that based on the predicted EC2 domain structure, the EC2 domain of Dsg2 peptide can be divided into six fragments, including EV10, KR20, IP10, VE10, YY15, and AQ15.

Figure 2:
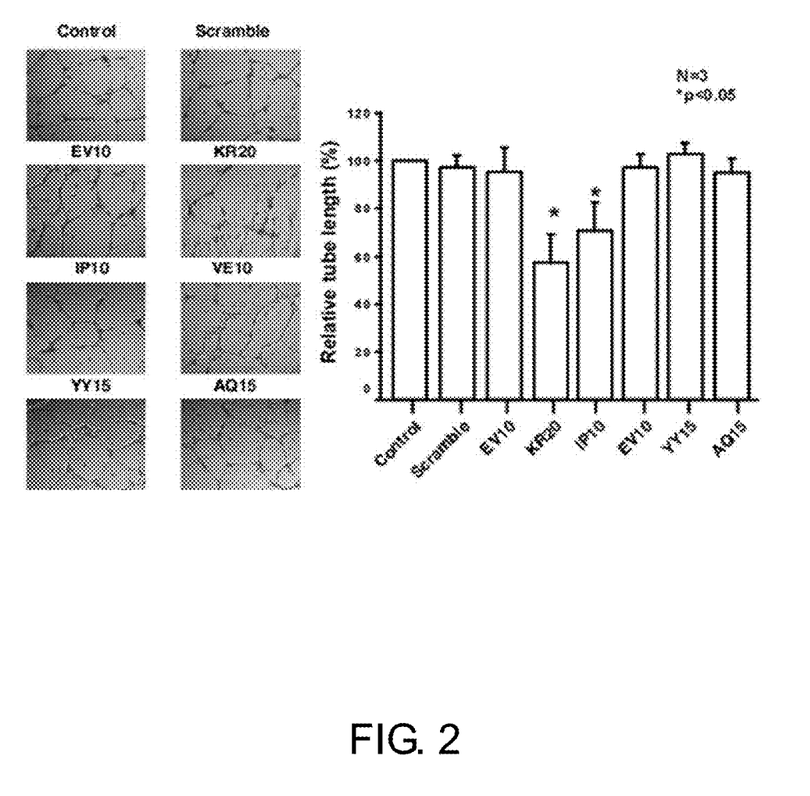

As depicted in FIG. 2, both the KR20 and IP10 fragments (1.0 mg/ml) can inhibit the angiogenesis of endothelial progenitor cells (EPCs) on the Matrigel (p<0.05), in which the KR20 fragment exhibited a more powerful effect on inhibiting tube formation. Accordingly, the present Dsg-2 peptide is derived from the KR20 fragment followed by conjugating with one extra cysteine amino acid residue; the forming peptide has an amino acid sequence of SEQ ID NO: 1.

Example 2 Dsg2-Derived Peptide Inhibits Angiogenesis in Endothelial Progenitor Cells The present Dsg-2 derived short peptide was evaluated in the Matrigel angiogenesis model to determine its anti-angiogenic efficacy on EPCs.

Figure 3:
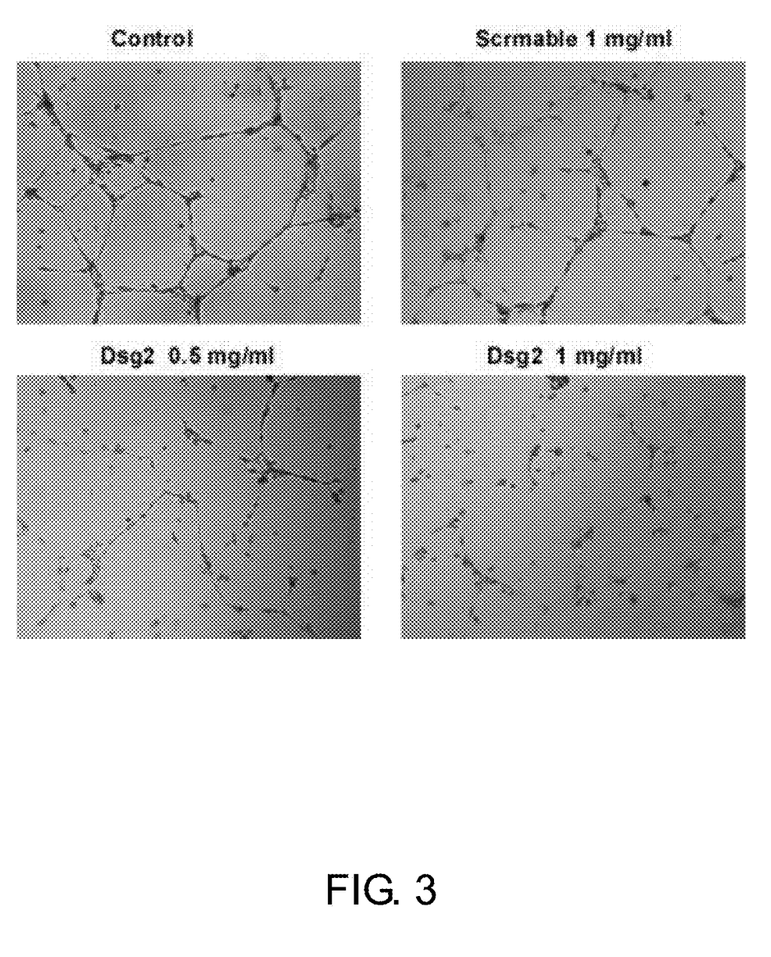
Figure 4:
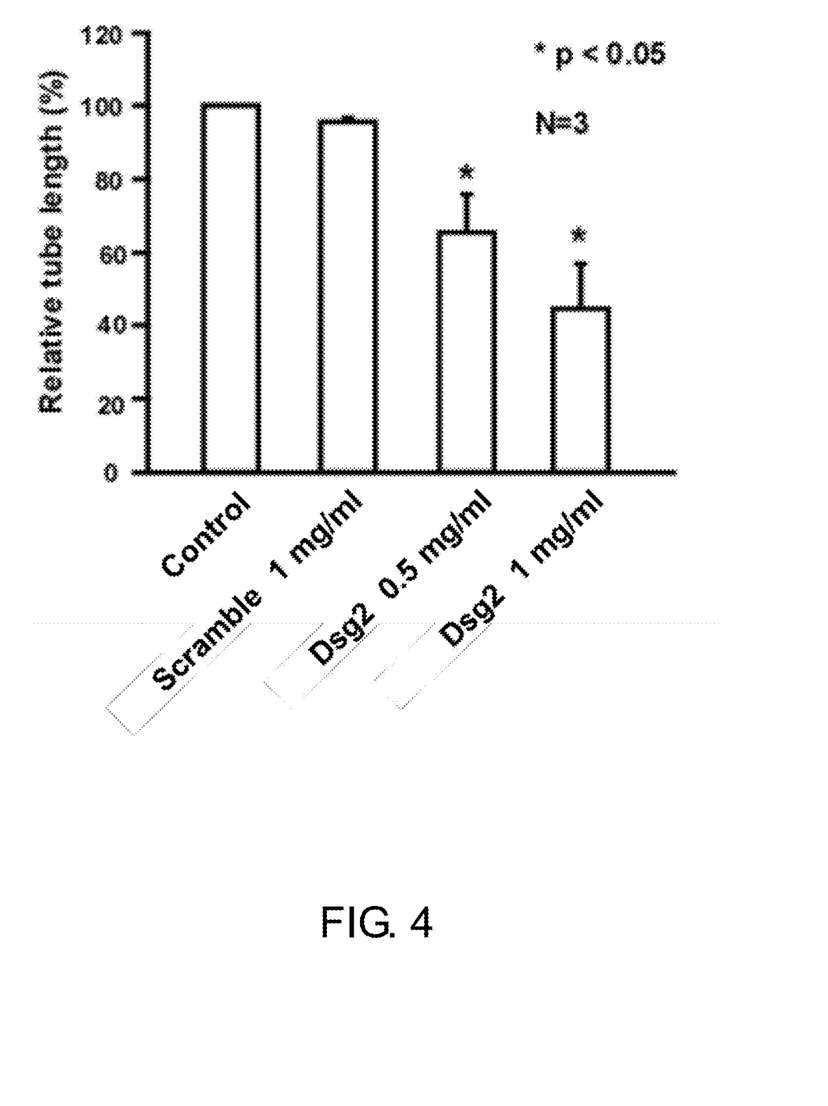

The result, as depicted in FIGS. 3 and 4, indicated that the present Dsg2-derived short peptide significantly inhibited angiogenesis in EPCs at concentrations of 0.5 mg/ml (200 uM) and 1.0 mg/ml (400 uM). In particular, at 1.0 mg/ml (400 uM), the Dsg2-derived short peptide elicited a reduction of tube formation by more than 50%, thereby resulting in a relative tube length of less than 50% in relative to the control group (p<0.05).

Example 3 Dsg2-Derived Peptide Inhibits Angiogenesis in Human Umbilical Vein Endothelial Cells The present Dsg-2 derived short peptide was evaluated in the Matrigel angiogenesis model to determine its anti-angiogenic efficacy on human umbilical vein endothelial cells (HUVECs). In this example, Avastin, a clinically used anti-angiogenic agent for treating cancer, was also used to investigate the efficacy of the present Dsg-2 derived short peptide.

Figure 5:
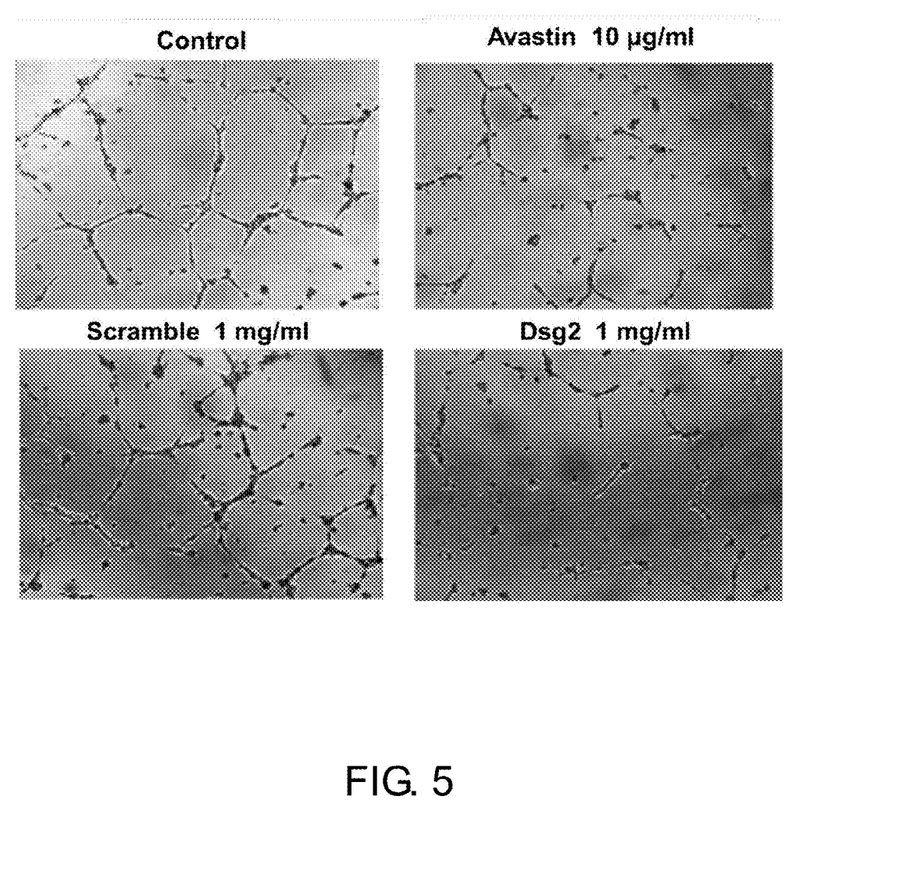
Figure 6:
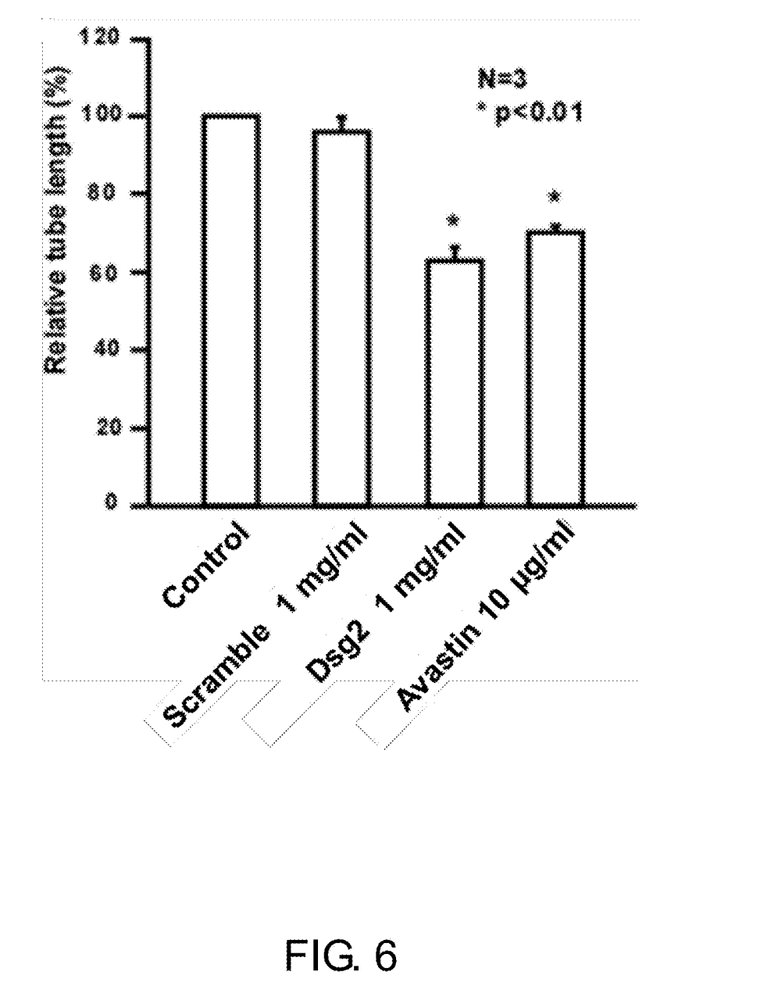

The data in FIGS. 5 and 6 indicated that the present Dsg2H derived short peptide, and the Avastin were capable of inhibiting angiogenesis of HUVEC cells on the Matrigel, whereas the scramble peptide was not. It should be noted that the present Dsg2-derived short peptide was more effective than Avastin in inhibiting tube formation, which suggests that the present Dsg2-derived short peptide is a potential therapeutic drug for treating retinal neovascular disease by inhibiting angiogenesis.

Example 4 Dsg2N Derived Peptide Inhibits Angiogenesis in Matrigel Plug

The antiH angiogenic efficacy of the present DsgH 2 derived short peptide was further examined by Matrigel plug assay. Generally, the Matrigel plug assay is a simple in vivo technique used to detect the newly formed blood vessels in the transplanted gel plug in mice, and thus could be used to evaluate the efficacy of both proH angiogenic and antiH angiogenic compounds in vivo.

Figure 7:
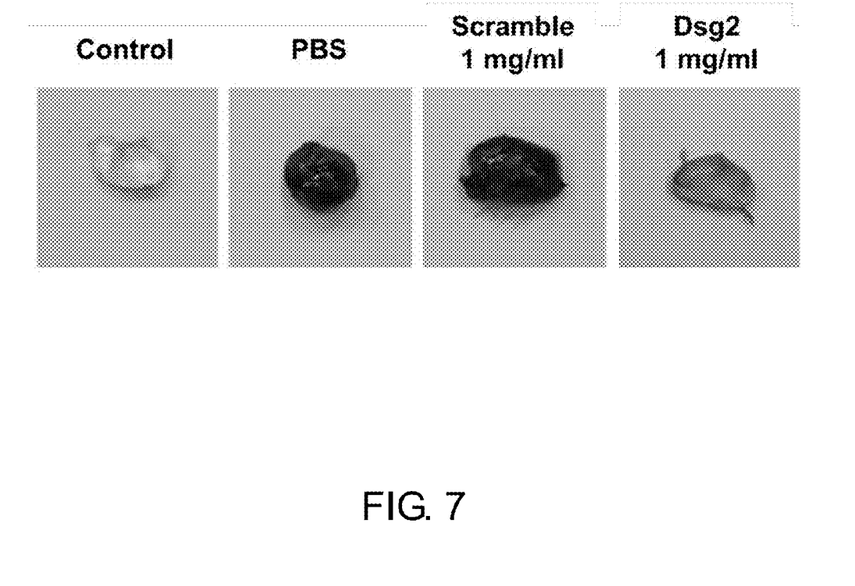
Figure 8:
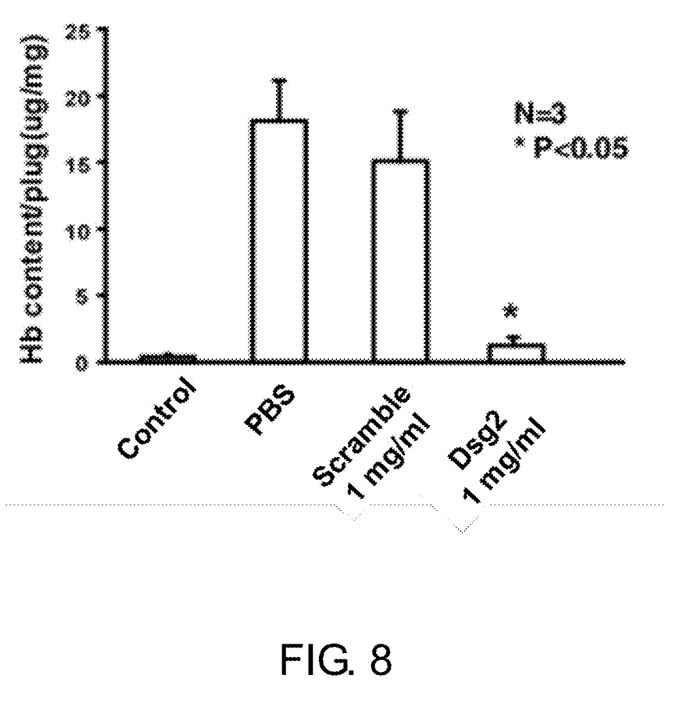

The data in FIG. 7 indicated that compared with PBS or scramble peptide control, the present Dsg2-derived short peptide was capable of inhibiting the formation of newly formed blood vessels in Matrigel plug. The analytic result in FIG. 8 further demonstrated that the hemoglobin content of Matrigel plug containing the present Dsg2-derived short peptide was significantly lower than that of Matrigel plug containing either PBS or scramble peptide (p<0.05).

Example 5 Dsg2N Derived Peptide Inhibits Angiogenesis in Animals with Oxygen-Induced Retinopathy (OIR)

Retinal hypoxia has been considered to be a major causative factor in the development of retinal neovascularization, a condition associated with blindness and vision loss in a variety of retinopathies. In this example, the anti-angiogenic efficacy of the present Dsg2-derived short peptide was evaluated by an animal model (a model used to mimic the hypoxia condition), in which the mice were first incubated in a hyperoxia condition and then transferred into a normoxia condition (relative hypoxia) so as to develop the oxygen-induced neovascularization followed by the specified treatments. The results were analyzed by a fluorescein-conjugated isolectin B4, which recognizes and specifically binds to the endothelial cells.

Figure 9:
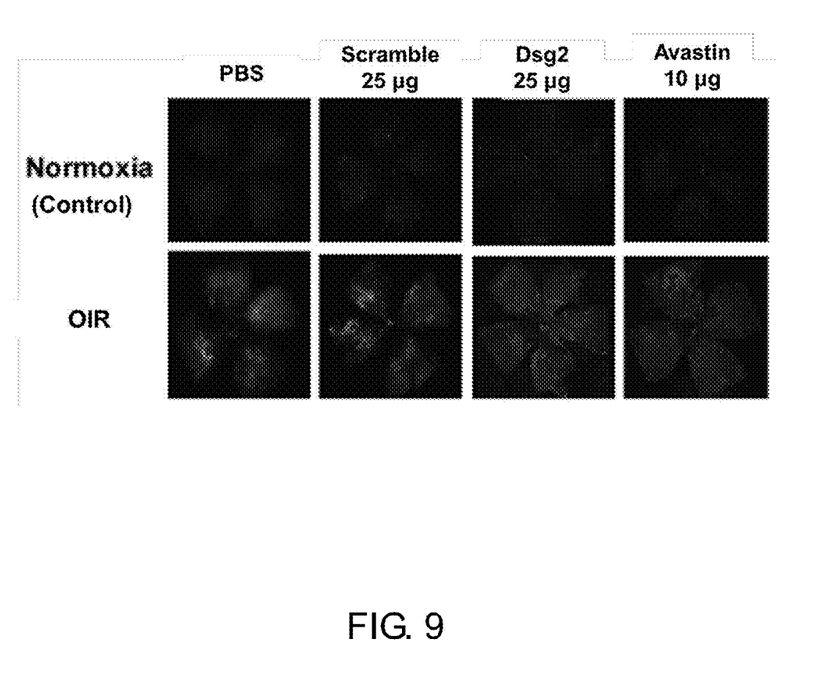
Figure 10:
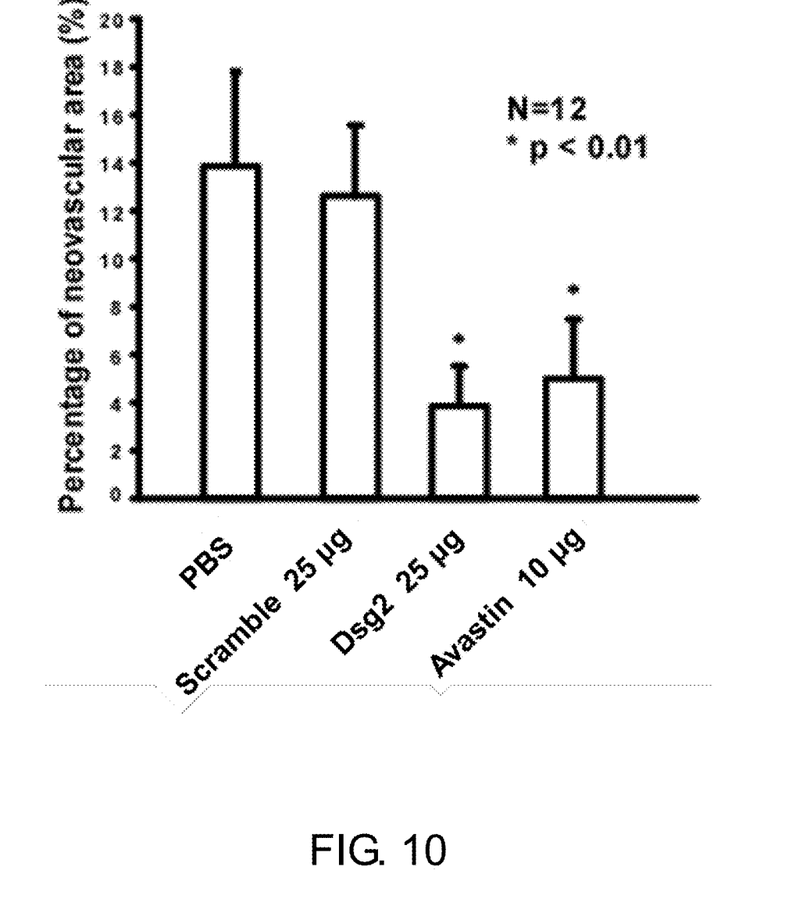

The data of FIGS. 9 and 10 indicated that the mice of OIR group developed neovascularization in retina, while the mice of control group (kept in normoxia condition) did not. Further, compared with PBS or scramble peptide control, both the present Dsg2H derived short peptide and Avastin significantly inhibited the angiogenesis in the OIR model (p<0.01). It is worth noting that the anti-angiogenic efficacy of the present Dsg2-derived short peptide was better than that of Avastin.

In sum, it was found that that the present Dsg2H derived short peptide is effective in inhibiting angiogenesis both in vitro and in vivo. It was also found that anti-angiogenic efficacy of the present Dsg2-derived short peptide is comparable to that of commercially available anti-angiogenic agents. Since angiogenesis is involved in numerous conditions and/or diseases, the present medicament and/or method are suitable for treating these conditions and/or disease by inhibiting angiogenesis.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating an angiogenesis-related condition and/or disease in a subject in need thereof, comprising administering to the subject a peptide comprising the sequence of SEQ ID NO: 1 in a therapeutically effective amount to ameliorate or alleviate symptoms associated with the angiogenesis-related condition and/or disease of the subject, wherein the angiogenesis-related condition and/or disease is or is caused by retinal neovascular disease, breast carcinoma, melanoma, or prostate cancer.

2. The method of claim 1, wherein the angiogenesis-related condition and/or disease.

3. The method of claim 1, wherein the angiogenesis-related condition and/or disease is breast carcinoma.

4. The method of claim 1, wherein the subject is a human.

* * * * *